US00PP13504P2

(12) United States Plant Patent
Zaiger et al.

(10) Patent No.: US PP13,504 P2
(45) Date of Patent: Jan. 21, 2003

(54) APRICOT TREE NAMED 'BRITTANY GOLD'

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 10/081,283

(22) Filed: Feb. 25, 2002

(51) Int. Cl.[7] ..... A01H 5/00
(52) U.S. Cl. ..... Plt./186
(58) Field of Search ..... Plt./186

*Primary Examiner*—Bruce R. Campell
*Assistant Examiner*—Anne Marie Grünberg

(57) ABSTRACT

A new and distinct variety of apricot tree (*Prunus armeniaca*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consists of the following combination of desirable features.

1. Heavy and regular production of fruit.
2. Fruit with a high degree of soluble solids, average Brix 18°.
3. Fruit that has firmer flesh than most standard commercial apricots in California.
4. Vigorous, semi-upright growth of tree.
5. Fruit with very good flavor and eating quality.
6. Fruit with an attractive, uniform, yellow skin color.

1 Drawing Sheet

STATEMENT REGARDING FEDERALLY SPONSORED RESEARCH OR DEVELOPMENT

Not applicable.

BACKGROUND OF THE INVENTION

Field of the Invention

In the field of plant genetics, we conduct an extensive and continuing plant-breeding program including the organization and asexual reproduction of orchard trees, and of which almonds, apples, plums, peaches, nectarines, apricots, cherries and interspecifics are exemplary. It was against this background of our activities that the present variety of apricot tree was originated and asexually reproduced by us in our experimental orchard located near Modesto, Stanislaus County, Calif.

Prior Varieties

Among the existing varieties of apricot trees (*Prunus armeniaca*), which are known to us, and mentioned herein, are 'Tri Gem' Apricot (U.S. Plant Pat. No. 6,765), 'Modesto' Apricot (U.S. Plant Pat. No. 2,543) and 'King' Apricot (non-patented).

STATEMENT REGARDING FEDERALLY SPONSORED RESEARCH OR DEVELOPMENT:

Not applicable.

ORIGIN OF THE VARIETY

The present new and distinct variety of apricot tree (*Prunus armeniaca*) was developed by us in our experimental orchard located near Modesto, Calif. as a first generation cross between proprietary lines of immediate parents, 20ED49 and 80GE216. The maternal parent 20ED49 originated from an open pollinated seedling of 'Tri Gem' Apricot (U.S. Plant Pat. No. 6,765) crossed with a seedling selected from a cross of 'Modesto' Apricot (U.S. Plant Pat. No. 2,543) with a late maturing seedling of unknown parentage. The pollen parent 80GE216 originated from a cross of 'King' Apricot (non-patented) crossed with a seedling of unknown parentage. We planted and grew a large number of these first generation seedlings, growing on their own root system, under close and careful observation, during which time the present variety exhibited distinct and desirable fruit characteristics and, in 1992, was selected for asexual reproduction and commercialization.

ASEXUAL REPRODUCTION OF THE VARIETY

Asexual reproduction of the new and distinct variety of apricot tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

Our present new and distinct variety of apricot tree *Prunus armeniaca*) is of large size, vigorous, semi-upright growth and a productive and regular bearer of medium size, yellow flesh, freestone fruit with very good flavor and eating quality. The fruit is further characterized by having firm flesh with good storage and shipping quality, having high soluble solids with average Brix of 18° and being relatively uniform in size throughout the tree. In comparison to its parent 'Tri Gem' Apricot (U.S. Plant Pat. No. 6,765), it is similar in size and firmness and is approximately 35 days later in maturity. In comparison to 'Modesto' Apricot (U.S. Plant Pat. No. 2,543), the new variety has firmer flesh, higher soluble solids, (Brix), and is approximately 30 days later in maturity.

PHOTOGRAPH OF THE VARIETY

The accompanying color photographic illustration shows typical specimens of the foliage and fruit of the present new apricot variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of apricot tree, its flowers, foliage and fruit, as based on observations of 6 year old specimens grown near Modesto, Calif., with color in accordance with Munsell Book of Color.

Tree:

*Size.*—Large. Tree pruned to 3 to 3.5 meters in height and width at maturity, primarily for economical harvesting of fruit.

*Vigor.*—Vigorous, growing 1.5 to 2 meters in height the first growing season. Varies with fertility of soil, climatic conditions and cultural practices.

*Form.*—Usually pruned to vase shape.

*Branching habit.*—Semi-upright with crotch angle of approximately 40 degrees. At maturity, heavy crop load increases spreading and crotch angle.

*Productivity.*—Productive. Usually sets 1½ to several times more fruit than desired, thinning and spacing of fruit necessary for marketable size.

*Bearer.*—Has set adequate fruit 4 consecutive years, no alternate bearing observed.

*Fertility.*—Believed to be self fertile, sets fruit heavy under bags without bee activity.

*Density.*—Medium dense. Pruned to vase shape to increase air and sunlight to center of tree to enhance fruit color, Brix and health of fruit wood.

*Hardiness.*—Hardy in all stone fruit growing areas of California. Tree grown in USDA Hardiness Zone 9. Estimated winter chilling requirement of 700 hours at or below 45° F.

Trunk:

*Size.*—Large. Average circumference 40.6 cm at 30.5 cm above ground on a 6 year old tree.

*Stocky.*—Medium stocky.

*Texture.*—Medium rough, increases with age of tree.

*Color.*—Varies from 2.5YR 4/4 to 5YR 3/2.

Branches:

*Size.*—Medium. Average circumference 22.9 cm at 1 meter above ground on a 6 year old tree.

*Surface texture.*—New growth smooth. Mature growth medium rough, roughness increases with age.

*Lenticels.*—Average number of 34 in a 25.8 square cm surface. Average length 1.2 mm. Average width 0.8 mm. Color varies from 5YR 7/4 to 5YR 7/6.

*Color.*—New growth 5R 4/6. Mature growth 2.5YR 4/4, becomes darker with age.

Leaves:

*Size.*—Medium. Average length 67.3 mm. Average width 59.8 mm.

*Form.*—Ovate.

*Apex.*—Cuspidate.

*Base.*—Obtuse.

*Margin.*—Serrate.

*Thickness.*—Medium.

*Surface texture.*—Upper surface relatively smooth with slight indentations over midrib and pinnate venation, glabrous. Lower surface relatively smooth with slight ridging from midvein and pinnate venation, glabrous.

*Petiole.*—Average length 22.5 mm. Average width 1.1 mm. Slightly grooved longitudinally. Glabrous. Color 5R 3/8 to 2.5GY 6/6, varies with amount of exposure to direct sunlight.

*Glands.*—Globose. Small. Average length 0.6 mm. Average diameter 0.4 mm. Number varies from 2 to 4, average 3. Located on upper portion of petiole and lower portion of leaf blade. Color varies from 5R 2/8 on upper portion to 2.5GY 7/6 on lower edge.

*Color.*—Upper surface 5GY 3/6. Lower surface 5GY 4/4. Midvein color — 5GY 7/4.

Flower buds:

*Size.*—Large. Average length 14.9 mm. Average diameter 7.7 mm.

*Hardiness.*—Hardy in all stone fruit growing areas of California.

*Form.*—Plump, conical.

*Pedicel.*—Average length 1.8 mm. Average width 1.6 mm. Color 2.5GY 7/8.

*Pubescence.*—Glabrous.

*Color.*—7.5RP 9/2.

*Number of buds per spur.*—Usually 5, varies from 4 to 9.

Flowers:

*Size.*—Large. Average height 15.1 mm. Average diameter 25 mm.

*Petals.*—Number — 5, alternately arranged to sepals. Orbicular, narrows at point of attachment. Average length 12.7 mm. Average width 13 mm. Color 5R 9/2 to 7.5R 9/2, color fades with age. Margin — entire, slightly cupped near apex.

*Sepals.*—Number — 5 alternately arranged to petals. Triangular, apex slightly pointed. Both surfaces glabrous. Average length 4.7 mm. Average width 3.6 mm. Color — upper surface varies from N/9.5 to 10RP 4/10. Lower surface 10RP 4/12.

*Stamens.*—Average number per flower 32. Average filament length 8.2 mm. Filament color N9/.5. Anther color 3.75Y 8.5/12.

*Pollen .*—Abundant, believed self fertile, set fruit under bag. Color 3.75Y 8.5/12.

*Pistil.*—Usually one. Average length 15.8 mm. Pubescent. Stigma is approximately 2.3 mm higher than anthers. Color 7.5Y 9/4.

*Fragrance.*—Moderate aroma.

*Blooming period.*—Date of First Bloom Feb. 25, 2001. Date of Petal Fall Mar. 6, 2001. Varies slightly with climatic conditions.

*Color.*—5R 9/2 to 2.5R 9/2.

*Number of flowers per flower bud.*—Usually 1.

*Pedicel.*—Average length 2.2 mm. Average width 1.8 mm. Color 2.5GY 7/6.

Fruit:

*Maturity when described.*—Firm ripe.

*Date of first picking.*—Jul. 8, 2001.

*Date of last picking.*—Jul. 14, 2001. Varies slightly with climatic conditions.

*Size.*—Medium. Average diameter axially 46.2 mm. Average transversely in suture plane 43 mm. Average weight 64.37 grams. Average weight varies slightly with fertility of the soil, amount of thinning and climatic conditions.

*Form.*—Globose, slightly flattened at apex and base.

*Suture.*—Shallow, extends from base to apex.

*Ventral surface.*—Slightly lipped, tightly closed.

*Apex.*—Varies from flat to slightly retuse.

*Base.*—Retuse.

*Cavity.*—Rounded to slightly elongated in suture plane. Average depth 4.6 mm. Average diameter 6.1 mm.

Stem:

*Size.*—Short. Average length 3.7 mm. Average diameter 2.4 mm.

*Color.*—2.5GY 7/6 to 2.5GY 7/8.

Flesh:

*Ripens.*—Evenly.

*Texture.*—Firm, smooth, apricot texture.

*Fibers.*—Few, small, tender.

*Firmness.*—Firm. Firmer than most commercial varieties of apricots. Holds firmness when fully tree ripe.

*Aroma.*—Moderate.

*Amydgalin.*—Undetected.

*Eating quality.*—Very good.

*Flavor.*—Very good. Good balance between acid and sugar.

*Juice.*—Moderate amount, enhances flavor.

*Brix.*—Average 18°. Varies slightly with amount of fruit per tree and climatic conditions.

*Color.*—7.5YR 7/10 to 7.5YR 7.12. Pit cavity. — 7.5YR 7/8 to 7.5YR 7.10.

Skin:

*Thickness.*—Medium.

*surface.*—Smooth.

*Pubescence.*—Pubescent, very short, fine, does not roll.

*Tendency to crack.*—None.

*Color.*—7.5YR 7/8 to 7/5YR 7/10. Uniformly yellow.

*Tenacity.*—Tenacious to the flesh.

Stone:

*Type.*—Freestone.

*Size.*—Medium. Average length 23.4 mm. Average width 17.8 mm. Average thickness 14.1 mm.

*Form.*—Ovoid.

*Base.*—Varies from rounded to slightly concaved.

*Apex.*—Rounded, no sharp point.

*Surface.*—Lightly pitted throughout. One shallow groove on each side of suture creating a small, narrow ridge.

*Sides.*—Equal.

*Tendency to split.*—None.

*Color.*—2.5YR 4/4, when dry.

Kernal:

*Form.*—Ovate.

*Taste.*—Bitter.

*Viability.*—Viable. Complete embryo development.

*Size.*—Average length 16.9 mm. Average width 11.8 mm. Average thickness 11.8 mm.

*Skin color.*—7.5YR 5/8, when dry.

Use: Dessert. Market — local and long distance.

Keeping quality: Good, held firm 2 weeks in cold storage at 38° F. to 42° F. without shriveling, internal breakdown of flesh or appreciable loss of flavor.

Shipping quality: Good, showed minimal skin scarring or bruising of flesh in picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of apricot tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct apricot tree, substantially as illustrated and described, characterized by its large size, semi-upright growth and being a productive and regular bearer of yellow flesh, freestone fruit having very good flavor and eating quality, having firm flesh with good handling and shipping quality and, in comparison to the fruit of the 'Modesto' Apricot (U.S. Plant Pat. No. 2,543), the new fruit has firmer flesh, higher Brix and is approximately 30 days later in maturity.

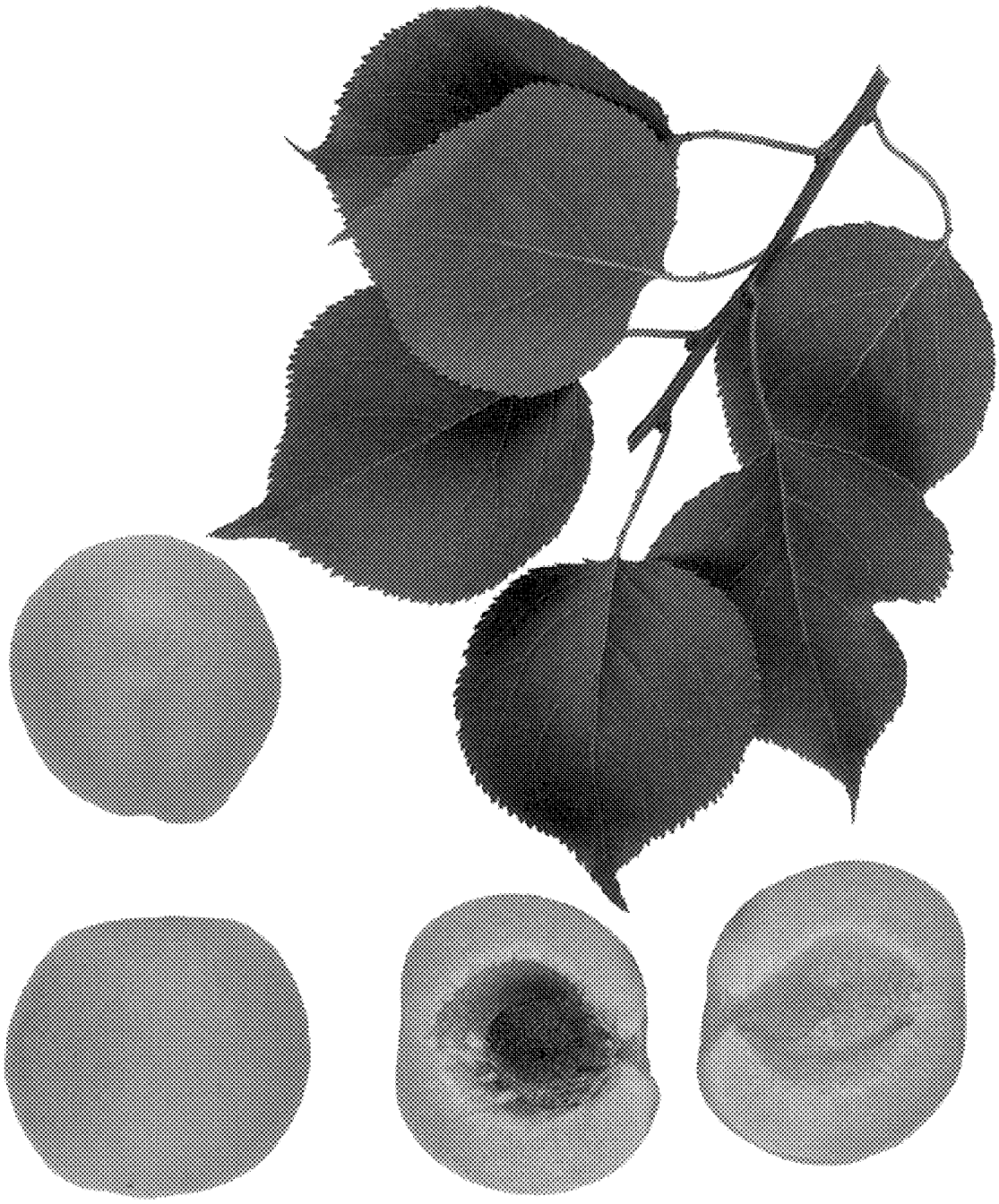

* * * * *